United States Patent [19]

Krijnen et al.

[11] 4,435,582
[45] Mar. 6, 1984

[54] MANUFACTURE OF MACROCYCLIC POLYETHERS

[75] Inventors: Wilhelmus J. Krijnen; Paulus A. M. Grotenhuis, both of Amsterdam, Netherlands

[73] Assignee: Shell Oil Company, Houston, Tex.

[21] Appl. No.: 252,648

[22] Filed: Apr. 9, 1981

[30] Foreign Application Priority Data

Jun. 11, 1980 [GB] United Kingdom ................ 8019112

[51] Int. Cl.³ .................... C07D 323/00; C07D 319/12
[52] U.S. Cl. .................................... 549/352; 549/347; 549/353; 549/377
[58] Field of Search .......................... 260/338, 340.3; 549/347, 352, 353, 377

[56] References Cited

U.S. PATENT DOCUMENTS 4,172,083 10/1979 Cincotta et al. .................... 260/338

OTHER PUBLICATIONS

Johns et al., Synthesis, 1976, pp. 515–516.
Lin et al., J. Chem. Soc. Chem. Comm., 1978, pp. 504–505.
Derwent Abstracts, 78278B/43, equivalent to Japanese Patent 54-119483.

Primary Examiner—Jane T. Fan
Attorney, Agent, or Firm—Dean F. Vance; Ronald R. Reper

[57] ABSTRACT

This invention deals with a process for the preparation of macrocyclic polyethers of the general formula:

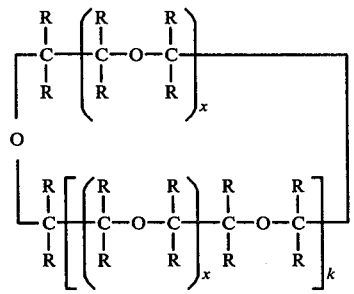

wherein x is 1–9; k is 0 or 1 and each R, which may be the same or different, represents a hydrogen atom or a lower alkyl or aryl group, or two R bonded to two adjacent carbon atoms form together with these carbon atoms a cyclic hydrocarbyl configuration, by reacting a compound of the general formula:

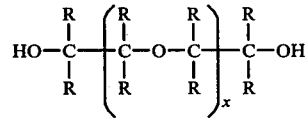

with a sulphonyl halide in the presence of a base and a halogen-containing solvent, preferably chlorobenzene. The process is of special interest for the manufacture of 18-crown-6.

8 Claims, No Drawings

MANUFACTURE OF MACROCYCLIC POLYETHERS

BACKGROUND OF THE INVENTION

1. Field of the Invention

The present invention relates to a process for the preparation of macrocyclic polyethers, commonly referred to as "crown ethers". The invention relates in particular to the preparation of 1,4,7,10,13,16-hexaoxacyclooctadecane, also known as 18-crown-6.

2. Description of the Prior Art

Synthetic macrocyclic polyethers are of great interest in that they contain intra-molecular cavities which are fit to accomodate alkali metal or alkaline-earth metal ions depending on the particular shape of the macrocyclic polyether applied. Therefore, salts of alkali metals and alkaline-earth metal ions, which are substantially insoluble, become solubilized in the presence of certain macrocyclic polyethers. It is also possible to dissolve such salts in organic solvents such as benzene or toluene in the presence of certain macrocyclic polyethers. Macrocyclic polyethers, and especially 18-crown-6, have found recognition as solvents for chemical reactions as well as phase-transfer catalysts for chemical reactions.

A number of synthetic techniques has been proposed for preparing macrocyclic polyethers. Among those, reference may be made to the catalytic oligomerization of ethylene oxide as described in U.S. Pat. No. 3,928,386 leading to mixtures of various macrocyclic polyethers. The reaction of tetraethyleneglycol with bis(2-chloroethyl) ether in the presence of potassium hydroxide and tetrahydrofuran without addition of water is described in "Synthesis" (1976) pages 515-516. However, even after reaction time of at least 18 hours, moderate yields are obtained and the working-up procedure includes a distillation or distillative decomposition of the macrocyclic polyether (complex) produced. It is further known from J. Chem. Soc. Chem. Comm., 1978, pages 504-505 that macrocyclic polyethers may be prepared by reacting (un)substituted polyethylene glycols having suitable ethylenoxy units with a sulphoxyl chloride in the presence of an alkali metal hydroxide in an aprotic solvent such as dioxane or dimethoxyethane, followed by pyrolysis of the salt complex obtained in order to liberate the macrocyclic polyether.

It is remarkable, however, that despite a fast growing interest in macrocyclic polyethers large scale preparations have not yet been reported.

SUMMARY OF THE INVENTION

It has now been found that macrocyclic polyethers can be prepared on a large scale without the serious disadvantage of either having to decompose a solid complex or to purify the product by distillation by carrying out the process in the presence of a halogen-containing solvent. The present invention therefore relates to a process for the preparation of macrocyclic polyethers according to the general formula:

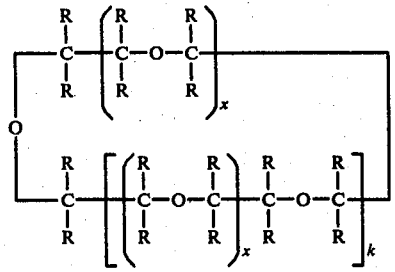

wherein x is an integer of from 1 to 9; k is 0 or 1, and each R, which may be the same or different, represents a hydrogen atom or a lower alkyl or aryl group, or two R bonded to two adjacent carbon toms form together with these carbon atoms a cyclic hydrocarbyl configuration. The process comprises reacting a compound according to the general formula:

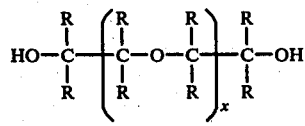

wherein x and R have the meaning as defined hereinbefore, with a sulphonyl halide in the presence of a base and a halogen-containing solvent.

The process according to the present invention is of special interest for the preparation of macrocyclic polyethers according to the general formula I wherein x is an integer of from 2 to 4 inclusive; k is 0 or 1 and each R, which may be the same or different, represents a hydrogen atom or a lower alkyl group, by reacting a compound according to the general formula II with a sulphonyl chloride in the presence of a base and a halogen-containing solvent. The process according to the present invention relates in particular to the preparation of 18-crown-6 by reacting triethylene glycol (formula II, x=3, and formula I, K=1) with a sulphonyl chloride in the presence of a base and a halogen-containing solvent.

It should be noted that the handleability of the reaction mixture is a key issue in the manufacture of large quantities of macrocyclic polyethers and that the use of oxygenated solvents such as tetrahydrofuran and dioxane gives rise to serious working-up problems, which do not occur or occur only to a minor degree in small-scale operations. They also require a solvent switch during the working-up procedure which is very unattractive and cause severe filtration problems. It is surprising that the use of a halogenated solvent enables the large scale preparation of macrocyclic polyethers to be carried out in an economically attractive manner.

DETAILED DESCRIPTION OF THE INVENTION

It will be appreciated that the process according to the present invention may occur via cyclization of a polyethylene glycol derivative originating from the appropriate polyethylene glycol as well as via cyclization of polyethylene glycol derivatives obtained from smaller polyethylene units which may have been subject to a condensation reaction. For instance, 18-crown-6 can be prepared starting from hexaethylene glycol but also starting from triethylene glycol or from mixtures containing triethylene glycol. It has been found in general that a polyethylene glycol having one oxygen atom more in the molecule than the macrocyclic polyether to be produced is to be preferred as a starting material over a lower polyethylene glycol unit having one oxygen atom more than half the amount of oxygen atoms present in the macrocyclic polyether to be produced.

Sulphonyl halides which can be used suitably in the process according to the present invention comprise alkyl, aryl, alkaryl and aralkyl sulphonyl chlorides and bromides containing up to 12 carbon atoms in the molecule. Preference is given to the use of alkyl sulphonyl halides, and especially of alkyl sulphonyl chlorides, having up to 6 carbon atoms in the molecule such as methane sulphonyl chloride and ethane sulphonyl chloride, as well as to aryl and alkaryl sulphonyl halides having up to 12 carbon atoms in the molecule such as benzene-sulphonyl chloride and toulene-p-sulphonyl chloride. Normally, the sulphonyl halide will be applied in the stiochiometrically required amount. A moderate excess of the sulphonyl halide, e.g. up to 50% on polyethylene glycol intake can be used advantageously.

Suitable bases which can be used in the process according to the present invention comprise inorganic bases such as lithium hydroxide, sodium hydroxide, potassium hydroxide, calcium hydroxide and barium hydroxide as well as mixtures of such bases. Also metal alkoxides, such as potassium t-butoxide or isopropoxide can be used. They can be applied as solids, e.g. in the form of pellets, powders or flakes. Preference is given to the use of powdered potassium hydroxide or potassium hydroxide/sodium hydroxide mixtures. Normally an excess of base is used in order to facilitate the reaction. Up to 5 times the molar amount of base can be used conveniently, amounts up to 3 times being preferred. Very large amounts of base should be avoided as this may lead to a thick, unstirrable reaction mixture.

Suitable halogen-containing solvents comprise polyhalogenated aliphatic hydrocarbons and halogenated aromatic hydrocarbons. Examples of halogenated aliphatic hydrocarbons include dichloromethane, dichloroethane, trichloroethane, tetrachloroethane, dibromoethane and tetrachloroethylene, preference being given to dichloromethane, Examples of halogenated aromatic hydrocarbons include chlorobenzene, bromobenzene, α-dichlorobenzene and m-dichlorobenzene. Preference is given to the use of halogenated aromatic compounds, and especially to the use of chlorobenzene since the use of this solvent has also considerable advantages in the working-up procedure of the crude macrocyclic polyether as will be explained hereinafter.

The amount of solvent to be used should be sufficient to ensure at least a workable reaction mixture. Amounts of solvent in the range of from 2 to 30 times the weight of the reactants can be suitably applied. Higher ratios can also be applied but they are not advantageous in that this would require the handling of very large quantities of solvent during the working-up procedure. Preference is given to a solvent:reactants weight ratio in the range of from 2 to 10.

The temperature at which the process according to the present invention is carried out is not critical. Normally, the reactions are slightly exothermic and can be conveniently carried out at room temperature or under gentle heating. Higher temperatures can also be applied when desired. The process is normally carried out under atmospheric or autogeneous pressure. Higher pressures can be applied but do not contribute substantially to the process.

The process according to the present invention can be operated batch wise or semi-continuously. It has been found convenient to add a mixture of the appropriate polyethylene glycol and the sulphonyl halide (if desired in the presence of small amount of the halogen-containing solvent) to a slurry containing the base in a finely divided form and the bulk of the halogen-containing solvent. If required, the reactants may also be added in stages and it is also possible to add a further quantity of the sulphonylhalide, if necessary in the halogen-containing solvent, after the exothermic reaction has subsided. It is also highly recommended to equip the reactor with an adequate stirring device and, if necessary, to add additional solvent so as to ensure the operability of the reaction mixture.

The reaction mixture obtained may be worked up in various manners. It is possible, for instance to isolate the macrocyclic polyethers produced in the form of suitable complexes by the addition of suitable complexing agents, which can then be separated from the reaction mixture by filtration. A number of solids will be entrained with the separated mass, however, so that an appropriate wash with a complexing agent such as nitromethane or acetonitrile will be necessary to obtain the macrocyclic polyether complex. But it is an implied disadvantage of this method that the complex formed to isolate the product has to be decomposed in order to liberate the macrocyclic polyether. This last step normally involves a distillation/re-complexation of the macrocyclic polyether produced and this is preferably to be avoided.

It has been found that a very convenient and attractive working-up procedure can be applied which comprises removal of at least part of the halogen-containing solvent, and especially of chlorobenzene, by distillation. The use of chlorobenzene has a further advantage in that water—produced during the reaction—is removed simultaneously in the form of the low-boiling chlorobenzene-water azeotrope which precedes the removal of chlorobenzene. Since the amount of halogenated solvent to be removed is much larger than the amount of water produced, the chlorobenzene-water removal also provides an almost quantitative removal of water from the reaction mixture. As the chlorobenzene-water azetrope is a heterogeneous azeotrope, any chlorobenzene obtained after the azeotropic drying can be easily separated from the water and can be recycled partly or totally to the reactor or the appropriate make-up stream. Normally, the azeotropic drying is carried out at atmospheric pressure at a temperature of about 135° C. The subjection of the reaction mixture to an advanced temperature during the azeotropic distillation has also the advantage that macrocyclic polyether complexes are decomposed in a very dilute system to give the free macrocyclic polyether without it being distilled as such. If desired, a filtration step can be incorporated after the azeotropic drying step to remove any solid materials. Finally, the remaining reaction mixture comprising predominantly the macrocyclic polyethers in the remainder of the halogen-containing solvent, is subjected to a distillation which can be carried out at reduced pressure in order to remove the solvent while leaving the macrocyclic polyether as the bottom product. The product may be used as such in many applications since any salts and/or solvent have been removed already.

In order to obtain the macrocyclic polyether in a very pure state, the product obtained may be subjected to a final purification procedure. Use can be made of purification methods known in the art, e.g., by complexation with acetronitrile or nitromethane, followed by isolation and decomposition of the complex obtained. Very good results can be obtained, depending to some extent on the macrocyclic polyether produced by using dimethyl oxalate or dimethylcarbonate, especially dimethyl oxalate.

The invention will now be illustrated by means of the following Examples, which are not meant to limit the invention:

EXAMPLE 1

A one-liter reactor equipped with a stirrer, a reflux condensor, a dropping funnel and a gas outlet tube was charged with chlorobenzene (650 grams (g)) and powdered potassium hydroxide (412.6 g). During two hours a mixture of triethylene glycol (39 g), methane sulphonyl chloride (31 g) and chlorobenzene (50 g) was added through the dropping funnel to the suspension obtained. The temperature of the reaction mixture rose to 45° C. Finally, a further mixture of methane sulphonyl chloride (6.3 g) and chlorobenzene (7 g) was added and the reaction mixture was kept under stirring for another hour.

Thereafter, the contents of the reaction was heated to reflux while azeotropically removing water produced during the reaction. During this azeotropic drying the temperature rose to 135° C. When no more water distilled the reaction mixture was allowed to cool to 40° C. The reaction mixture was then filtered in order to remove potassium chloride and potassium methane sulphaonate salts. The removed salts were washed with chlorobenzene (50 g). The filtrate was then subjected to a flash distillation under reduced pressure (0.2 kPa) in order to remove the solvent chlorobenzene. During the distillation the temperature rose to 110° C. A residue was obtained (35 g), containing uncoverted triethyleneglycol (8 g), and 18-crown-6 (13 g selectivity 45%) the remainder being heavy ends.

In order to obtain 18-crown-6 in a very pure state, the residue obtained hereinabove was dissolved in a mixture of methyl tertiary butyl ether (40 g) and isopropanol (8 g). After filtration, molten dimethyl oxalate (7 g) was added and the mixture kept for two hours at 5° C. During this time the 18-crown-6/dimethyl oxalate complex precipitated. It was filtered off and washed with a mixture of methyl tertiary butyl ether (85 g) and isopropanol (1 g). The complex thus obtained was subjected to pyrolysis to distill off the dimethyl oxalate at elevated temperature (110° C.–145° C.) and reduced pressure (0.3 kPa). As bottom product 18-crown-6 was obtained as a pure product (>99% w) in a yield of 11.2 g (76% calculated on crude product).

EXAMPLE 2

The experiment described in the previous Example was repeated using dichloromethane as the solvent (750 ml), twice the amount of potassium hydroxide and 1.6 times the amount of triethylene glycol and methane sulphonyl chloride, but in the absence of a further addition of the last two reactants. 18-crown-6 was obtained in a very pure state (>99% in a reasonable yield).

EXAMPLE 3

The experiment described in Example 1 was repeated on a larger scale. To a suspension of powdered potassium hydroxide (208 g) in chlorobenzene (3250 g) in a five-liter reactor was added at room temperature during two hours a mixture of triethyleneglycol (195 g) and methane sulphonylchloride (155 g) in chlorobenzene (250 g). During the addition the temperature gradually rose to 45° C. Thereafter a mixture of methane sulphonylchloride (31.5 g) in chlorobenzene (35 g) was added at once and the reaction mixture kept under stirring for another hour. After the azeotropic removal of water (about 85 g) the reaction product was worked up in the manner as described in Example 1, giving after the final pyrolysis of the 18-crown-6/dimethyloxalate complex at elevated temperature and reduced pressure, a residue of very pure 18-crown-6 (>99%) in a yield almost identical to that obtained in the experiment described in Example 1.

EXAMPLE 4

The experiment described in Example 3 was repeated on a kmol scale while recycling chlorobenzene obtained from the heterogeneous chlorobenzene/water azeotrope to the reactor. Due to the use of a halogenated solvent no problems with respect to handleability were encountered during the reaction procedure. The reaction mixture could be stirred efficiently during the reaction. During the various stages of this production run, samples were taken and analyzed which were in full agreement with the product compositions as detected in the earliest experiments described hereinbefore.

EXAMPLE 5

The experiment described in Example 1 was repeated using a commercially available polyethylene glycol (PEG 300) as the reactant together with a mixture of powdered sodium hydroxide and powdered potassium hydroxide in chlorobenzene. After the removal of water by azeotropical drying and the removal of the excess chlorobenzene by flash distillation, a mixture of crown-ethers ranging from 15-crown-5 to 27-crown-9 was obtained, the main product being 18-crown-6. This compound could be recovered almost quantitatively from the reaction products using dimethyloxalate as the complexing agent in the manner as described in Example 1.

What is claimed is:

1. A process for the preparation of macrocyclic polyethers according to the formula:

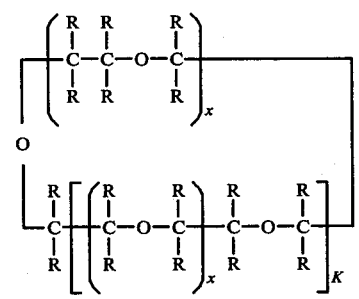

where x is an integer from 1 to 9, K is 0 or 1, and each R, which may be the same or different, represents a hydrogen atom or a lower alkyl group which process comprises reacting a compound according to the formula:

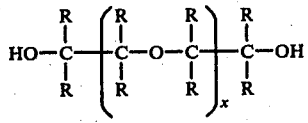

where x and R have the meaning as defined hereinbefore, with a sulphonyl halide in the presence of a base and a chlorobenzene solvent.

2. A process according to claim 1, where said sulphonylhalide is an alkyl, aryl, alkaryl or aralkylsulphonyl chloride or bromide.

3. A process according to claim 1, which comprises reacting said compound with a sulphonylchloride in the presence of an inorganic base.

4. A process according to claim 3, where said base is a powdered inorganic base.

5. A process according to claim 1, which also comprises the recovery of the macrocyclic polyether by removal of at least part of the water from the reaction mixture by azeotropic distillation.

6. A process according to claim 5, which comprises recycling at least part of the chlorobenzene solvent.

7. A process according to claim 1, where x is an integer from 2 to 4 inclusive.

8. A process according to claim 7, which comprises the preparation of 1-4-7-10-13-16-hexaoxacyclooctadecane by reacting triethyleneglycol and/or hexaethyleneglycol with a sulphonylchloride in the presence of a base and a chlorobenzene solvent.

* * * * *